(12) United States Patent
Demelo et al.

(10) Patent No.: US 7,501,093 B2
(45) Date of Patent: Mar. 10, 2009

(54) VIAL FOR TEST STRIPS

(75) Inventors: Erik Demelo, Douglaston, NY (US); Joseph Flaherty, Westford, MA (US); Timothy Golnik, Boxford, MA (US)

(73) Assignee: Agamatrix, Inc., Salem, NH (US)

( * ) Notice: Subject to any disclaimer, the term of this patent is extended or adjusted under 35 U.S.C. 154(b) by 331 days.

(21) Appl. No.: 11/252,959

(22) Filed: Oct. 18, 2005

(65) Prior Publication Data

US 2007/0084749 A1  Apr. 19, 2007

(51) Int. Cl.
B65D 81/26 (2006.01)
F17C 11/00 (2006.01)
G01N 33/00 (2006.01)
G01N 21/00 (2006.01)

(52) U.S. Cl. .............................. 422/58; 422/56; 436/92

(58) Field of Classification Search ............. 206/83, 206/204, 349, 438, 569; 134/135; 215/206; 435/283; 600/556; 436/92, 96, 98, 99; 422/58, 422/55, 61, 100, 102, 56, 99

See application file for complete search history.

(56) References Cited

U.S. PATENT DOCUMENTS

| 1,468,917 | A | * | 9/1923 | Osburn | 248/205.5 |
|---|---|---|---|---|---|
| 1,824,880 | A | * | 9/1931 | Forbes | 312/73 |
| 2,944,661 | A | * | 7/1960 | Goldstein | 134/137 |
| 3,066,687 | A | * | 12/1962 | Rohmann | 134/148 |
| 3,826,358 | A | * | 7/1974 | Butler et al. | 206/204 |
| D326,810 | S | * | 6/1992 | Ives | D3/264 |
| 5,142,710 | A | * | 9/1992 | Olson | 4/325 |
| 5,316,732 | A | | 5/1994 | Golukhov et al. | |
| 5,402,810 | A | * | 4/1995 | Donley | 134/135 |
| 5,429,804 | A | | 7/1995 | Sayles | |
| 5,788,064 | A | | 8/1998 | Sacherer et al. | |
| 6,213,777 | B1 | * | 4/2001 | Seitzinger | 433/229 |
| 6,557,484 | B1 | * | 5/2003 | Engelman | 116/206 |
| 6,872,358 | B2 | | 3/2005 | Hagen et al. | |
| 7,185,780 | B2 | * | 3/2007 | Nomula | 220/359.3 |
| 2005/0016873 | A1 | * | 1/2005 | Belfance et al. | 206/204 |

FOREIGN PATENT DOCUMENTS

| EP | 0289761 A2 | 11/1988 |
|---|---|---|
| WO | 95/07659 A1 | 3/1995 |
| WO | 97/33519 A1 | 9/1997 |

\* cited by examiner

*Primary Examiner*—Bryon P Gehman
*Assistant Examiner*—Ernesto A Grano
(74) *Attorney, Agent, or Firm*—Larson & Anderson, LLC (57) ABSTRACT

A diagnostic test strip vial has a container, a lid, and a plurality of diagnostic test strips. The container has a generally annular wall terminating at a base and at an open mouth. The lid has a top and a lifting tray connected to the top by a connector that is sufficiently long that the distance between the top and the lifting tray is at least as long as the length of a diagnostic test strip and sufficiently short that the top may engage the open mouth of the container to close the vial when the lifting tray is engaged with the inner side of the annular wall of the container. The test strips are disposed on the lifting tray which is sized to slidably engage the inner side of the annular wall of the container.

24 Claims, 13 Drawing Sheets

VIAL FOR TEST STRIPS

BACKGROUND OF THE INVENTION

Test strips for medical diagnostic purposes are typically supplied and carried in vials from which they are removed as required by a user, for example, when a diagnostic test is to be carried out. Typical types of test strips include those used for measuring analyte concentrations, such as glucose, in a human fluid, such as blood. Test strip vials should be user-friendly and inexpensive to make.

SUMMARY OF THE INVENTION

The present invention provides a user-friendly test strip vial that has a container with a generally annular wall terminating at a base and at an open mouth, a lid having a lifting tray and a top connected to the lifting tray by a connector, and a plurality of diagnostic test strips. Test strips are disposed on the lifting tray which is sized to slidably engage the annular wall of the container. The connector is sized so that the test strips may fit between the top and the lifting tray and also so that the top may engage the annular wall of the container to close the vial. When a user opens the vial, the lifting tray is raised from the container thereby lifting the test strips from a position closer to the bottom of the container to a position toward the open mouth.

One embodiment of the present invention provides a test strip vial comprising a container, a lid, and a plurality of diagnostic test strips, wherein: (i) the container comprises a generally annular wall terminating at a base and at an open mouth at an end opposite the base; (ii) the lid comprises a top and a lifting tray connected to the top by a connector, wherein: the lifting tray is sized to slidably engage the inner side of the annular wall of the container and the connector is sufficiently long that the distance between the top and the lifting tray is at least as long as the length of a diagnostic test strip and sufficiently short that the top may engage the open mouth of the container to close the vial when the lifting tray is engaged with the inner side of the annular wall of the container, and (iii) the test strips are disposed inside the container on the lifting tray. The vial may also optionally comprise a desiccant.

DETAILED DESCRIPTION OF THE INVENTION

It is often an advantage in the analyte detection industry to provide vials, test strips, and diagnostic meters that are as small as possible to allow a user to carry them with the utmost ease. However, the user of such items may be arthritic or have some other physical impairment which would hinder their ability to remove a single diagnostic test strip from a small vial. This physically impaired user may find it easier to dump the strips contained in the vial into their hand or onto another potentially contaminated surface in order to retrieve a single strip for performing a diagnostic test. Subsequently, the user may return potentially contaminated strips to the vial for storage and for future tests.

The present invention provides a user-friendly medical diagnostic test strip vial that allows a user greater access to the test strips contained in it. The vial has a container with a generally annular wall terminating at a base and at an open mouth, a lid having a lifting tray and a top connected to the lifting tray by a connector, and a plurality of diagnostic test strips. Test strips are disposed on the lifting tray which is sized to slidably engage the annular wall of the container. The connector is sized so that the test strips may fit between the top and the lifting tray and also so that the top may engage the annular wall of the container to close the vial. The connector may also have a hinge or be made of a flexible material so that the top may bend back giving a user greater access to the test strips. When a user opens the vial the lifting tray is raised from the container thereby lifting the test strips from a position closer to the bottom of the container to a position toward the open mouth.

One embodiment of the present invention provides a test strip vial comprising a container, a lid, and a plurality of diagnostic test strips, wherein: (i) the container comprises a generally annular wall terminating at a base and at an open mouth at an end opposite the base; (ii) the lid comprises a top and a lifting tray connected to the top by a connector, wherein: the lifting tray is sized to slidably engage the inner side of the annular wall of the container and the connector is sufficiently long that the distance between the top and the lifting tray is at least as long as the length of a diagnostic test strip and sufficiently short that the top may engage the open mouth of the container to close the vial when the lifting tray is engaged with the inner side of the annular wall of the container, and (iii) the test strips are disposed inside the container on the lifting tray. The vial may also optionally comprise a desiccant (e.g. a silica gel or a molecular sieve material).

Figure 1A:
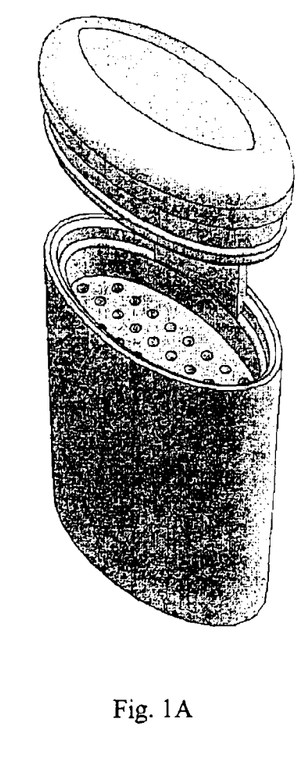
FIG. 1A is an isometric view of a vial in accordance with the present invention.
Figure 1B:
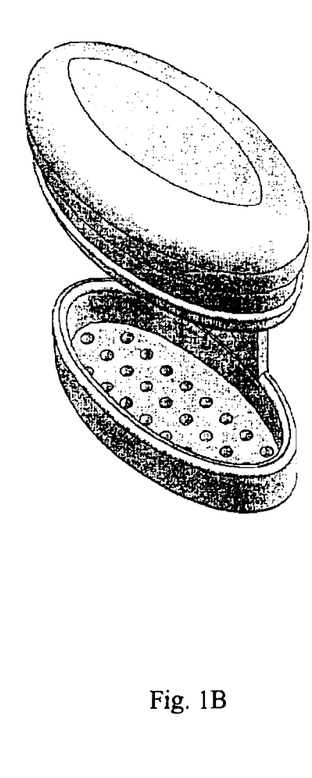
FIG. 1B is an isometric view of a lid having a top, a connector, and a lifting tray for a vial in accordance with the present invention.
Figure 1C:
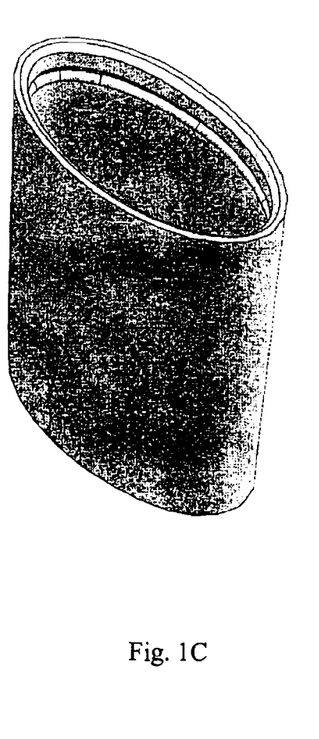
FIG. 1C is an isometric view of a container for a vial in accordance with the present invention.
Figure 1D:
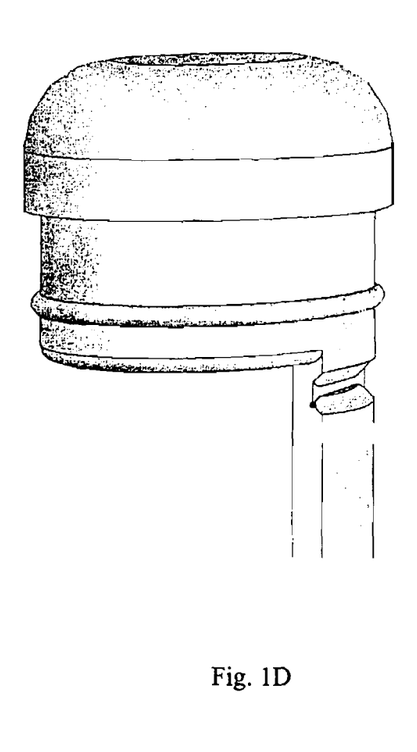
FIG. 1D is an isometric view of a lid with a hinge in accordance with the present invention.

FIGS. 1A through 1D show isometric views of an exemplary embodiment of a vial, without test strips, of the present invention. As depicted in FIG. 1A the vial has a lid (also shown in FIG. 1B) with a hinge disposed on the connector (as shown in FIG. 1D) and a container (also shown in FIG. 1C).

Simplified FIGS. 1E through 10 are provided to facilitate explanation of the various embodiments of the vial of the present invention.

Figure 1E:
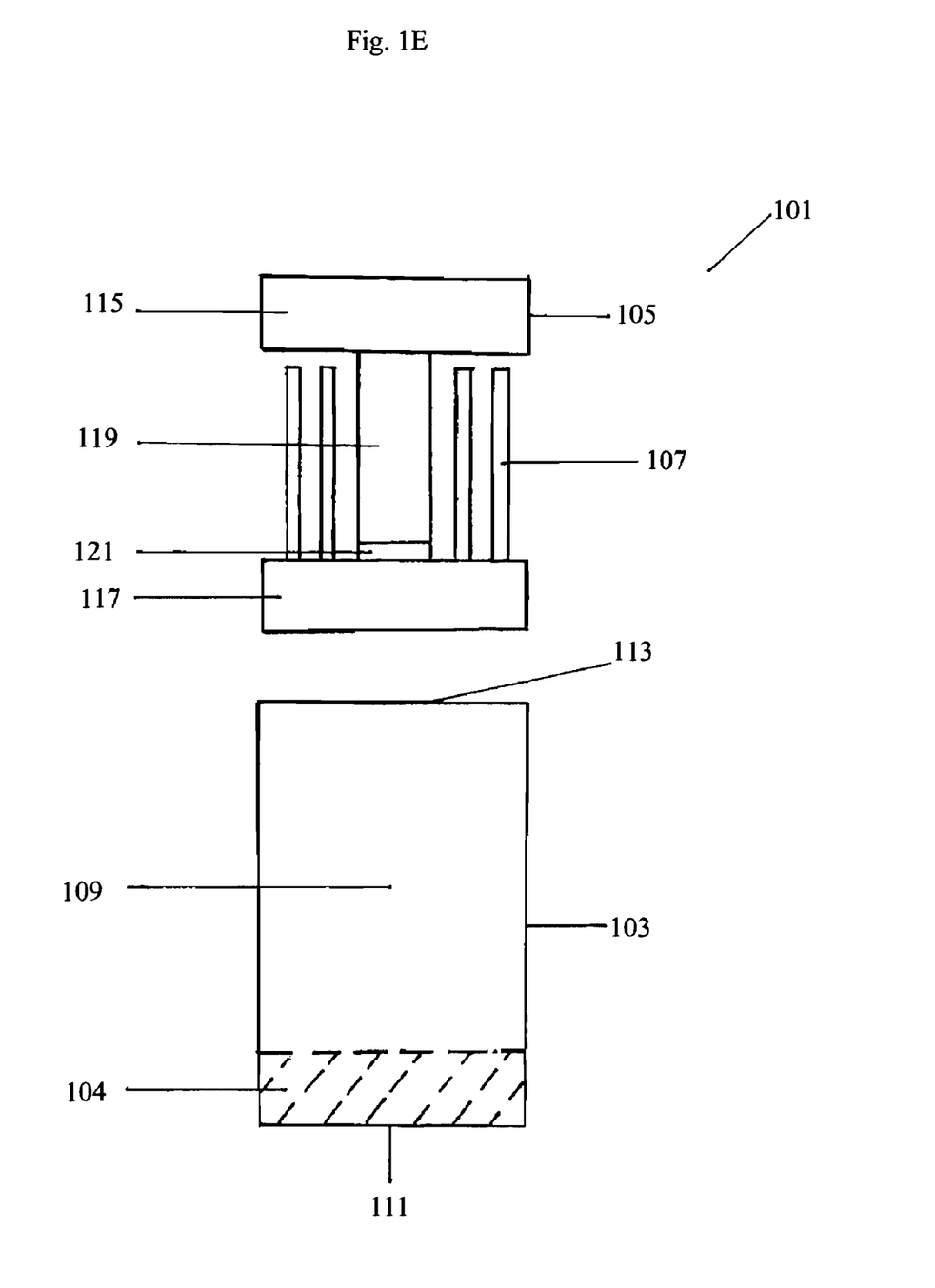
FIG. 1E is an exploded front elevation view of a vial in accordance with the present invention.

FIG. 1E depicts an embodiment of the present invention where a diagnostic test strip vial 101 has a container 103, a lid 105, and a plurality of diagnostic test strips 107. The container 103 has a generally annular wall 109 terminating at a base 111 and at an open mouth 113 at an end opposite the base 111. The lid 105 comprises a top 115 and a lifting tray 117 connected to the top 115 by connector 119. The lifting tray 117 is sized to slidably engage the inner side of the annular wall 109 of container 103. The connector 119 is sufficiently long that the distance between the top 115 and the lifting tray 117 is at least as long as the length of a diagnostic test strip 107 disposed on lifting tray 117, and sufficiently short that the top 115 may engage the annular wall 109 of the container 103 to close the vial 101 when the lifting tray 117 is engaged with the inner side of the annular wall 109. The connector 119 may optionally comprise a hinge 121 disposed between the top 115 and the lifting tray 117, for example somewhere in the middle of connector 119 or at the intersection of the connector 119 and the lifting tray 117 or the top 115. The hinge allows the top to be bent back from the container thereby giving a user greater access to the test strips contained in the vial. In FIG. 1A, hinge 121 is disposed at the junction of the connector 119 and the lifting tray 117.

Figure 1F:
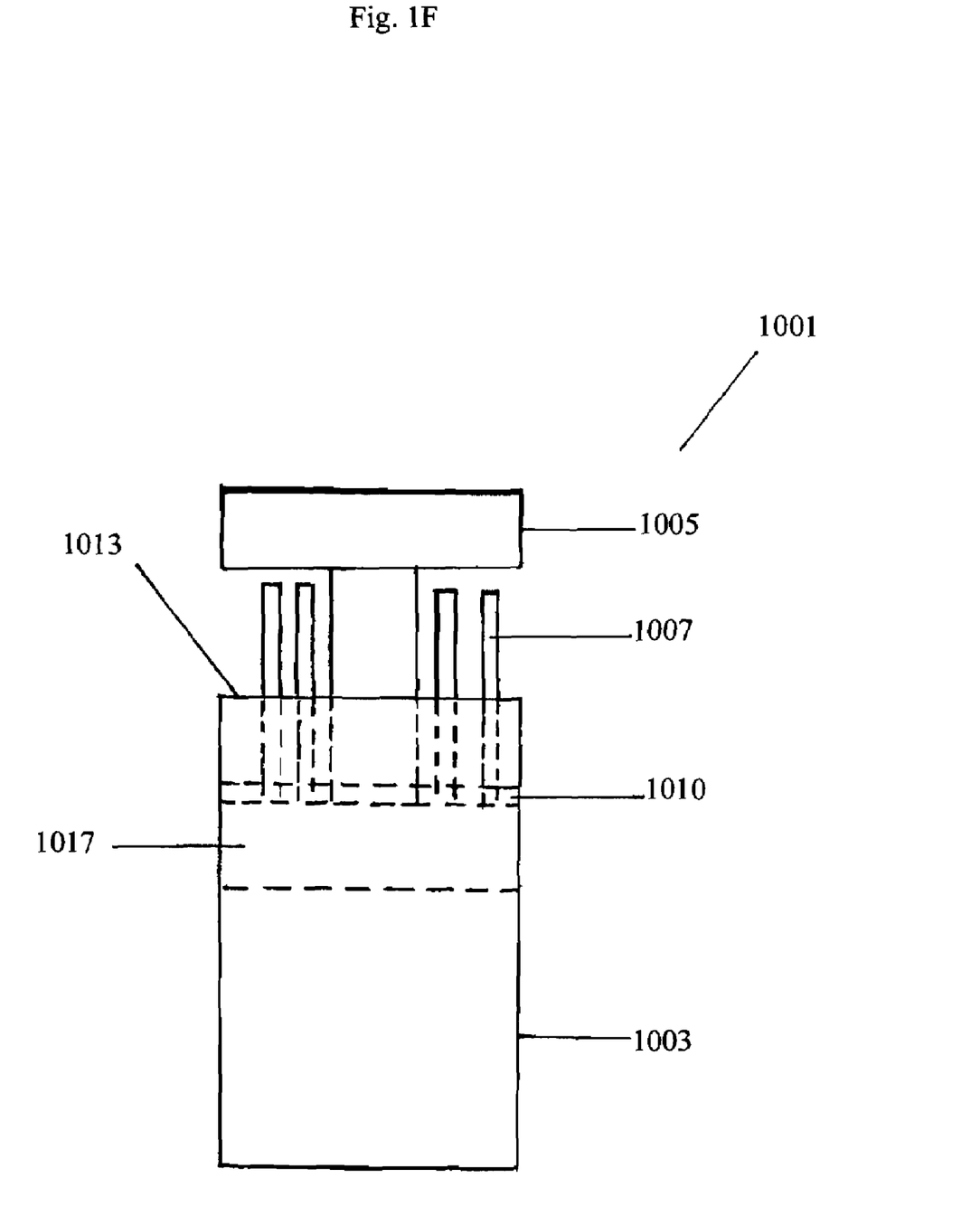
FIG. 1F is a front elevation view of a vial in accordance with the present invention.

When a user opens the vial of the present invention, lid 105 is moved away from base 111 of container 103 along the axis of annular wall 109. When this happens, lifting tray 117 and test strips 107 are moved from a position closer to the base 111 of container 103 to a position closer to the open mouth 113 so as to allow a user greater access to test strips 107. FIG. 1F illustrates a preferred embodiment, wherein when vial 1001 is open, test strips 1007 extend past the open mouth 1013 of the container 1003. FIG. 1F further illustrates an embodiment wherein stopping ridge 1010 provides a stopping end point and prevents lid 1005 from being fully removed from the container 1003 when lifting tray 1017 reaches stopping ridge 1010. The structure of the stopping ridge is not particularly limited, for example, it may be a continuous raised ridge disposed on the inner side of the annular wall of the container extending for the entire circumference of the annular wall or it may be a structure like a notch or a combination of notches that are disposed on the inner side of the annular wall.

The term "slidably engage" refers to the sizing of the lifting tray of the lid relative to the interior dimensions of the annular wall of the container. As used in the specification and claims of this application, the term "slidably engage" means that the lifting tray has the same general outer dimensions as the interior dimensions of the annular wall of the container and that it engages the annular wall with sufficient tightness so that a test strip cannot slip between the lifting tray and the container to the space below the lifting tray while still sliding into the container. In a preferred embodiment, the lifting tray may slide into the container with minimal force, for example the force applied by one hand of the user. In some embodiments, for example where the lifting tray is acting as a piston as depicted in FIGS. 3A and 3B, the fit between the lifting tray and the annular wall maybe sufficiently tight so as to ensure a stable humidity environment inside of a closed vial.

It is often preferred that medical diagnostic test strips be stored in an environment where there is a reduced moisture environment as compared to the normal atmosphere. To maintain this reduced moisture environment it is often desired that the space within the container is sealed from the outside atmosphere using a seal that seals the lid to the container. In addition to sealing the container from the surrounding environment a desiccant may be employed. Non-limiting examples of suitable desiccants include silica gel and molecular sieve material produced by CSP Technologies, Inc. The desiccant may be located in the container and/or in the lid (e.g. in or on the top, the lifting tray, the connector, or any combination thereof) such that it is in contact with the environment where the test strips are disposed, namely above the lifting tray. For example, as depicted in FIG. 1E, desiccant 104 is disposed within the container 103 below lifting tray 117. Lifting tray 117 maybe perforated to allow the passage of gasses through the lifting tray to/from the test strip area. In an embodiment where a molecular sieve material is used as a desiccant, it may be disposed on the inner side of the annular wall the container, the base of the container, the top, the lifting tray, the connector, or any combination thereof.

Figure 2A:
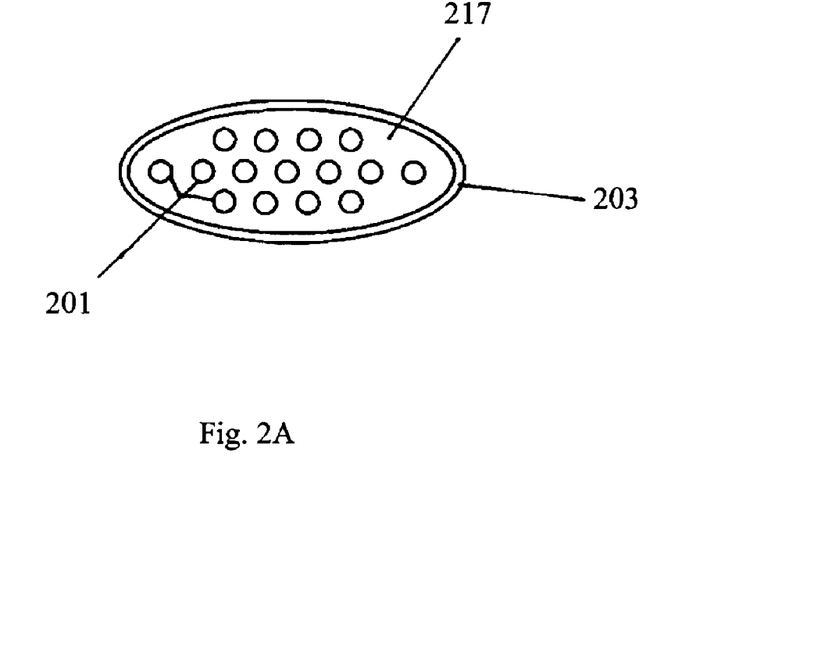
FIG. 2A is a top elevation view of a lifting tray in accordance with the present invention.
Figure 2B:
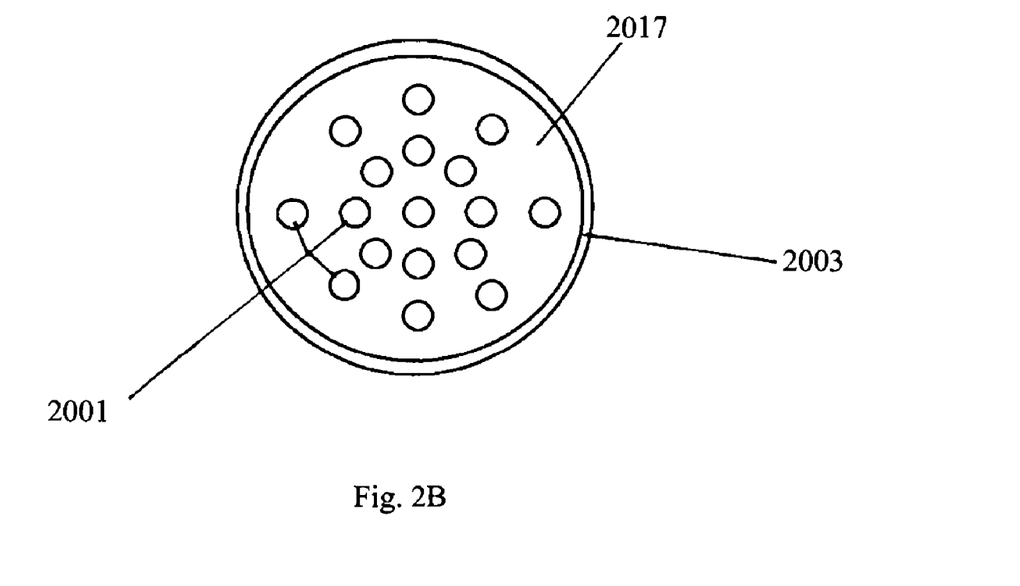
FIG. 2B is a top elevation view of a lifting tray in accordance with the present invention.

FIGS. 2A and 2B depict further embodiments of the lifting tray 217, 2017 of a vial of the present invention. As depicted in FIG. 2A lifting tray 217 is oval and is sized to slidably engage the inner side of an annular wall of a container, here an oval container 203. Further lifting tray 217 has holes 201 extending through lifting tray 217 so as to provide a passage for gases and/or vapors between the area beneath the lifting tray and the area above the lifting tray where the strips are disposed. FIG. 2B shows a circular embodiment of the lifting tray 2017 of the present invention for use with a circular container 2003. Lifting tray 2017 here further comprises optional holes 2001 extending through the lifting tray 2017. Holes 201, 2001 are sized to be large enough to provide a passage through the lifting tray of gases and/or vapors but small enough not to allow a test strip disposed on the lifting tray to pass through the lifting tray. In another embodiment the lifting tray may have a notched edge to provide a passage for gases and/or vapors between the area beneath the lifting tray and the area above the lifting tray where the strips are disposed. The notch or notches are sized to be large enough to provide a passage for gases and/or vapors between the areas above and below the lifting tray but small enough not to allow a test strip disposed on the lifting tray to pass through the notch.

Figure 3A:
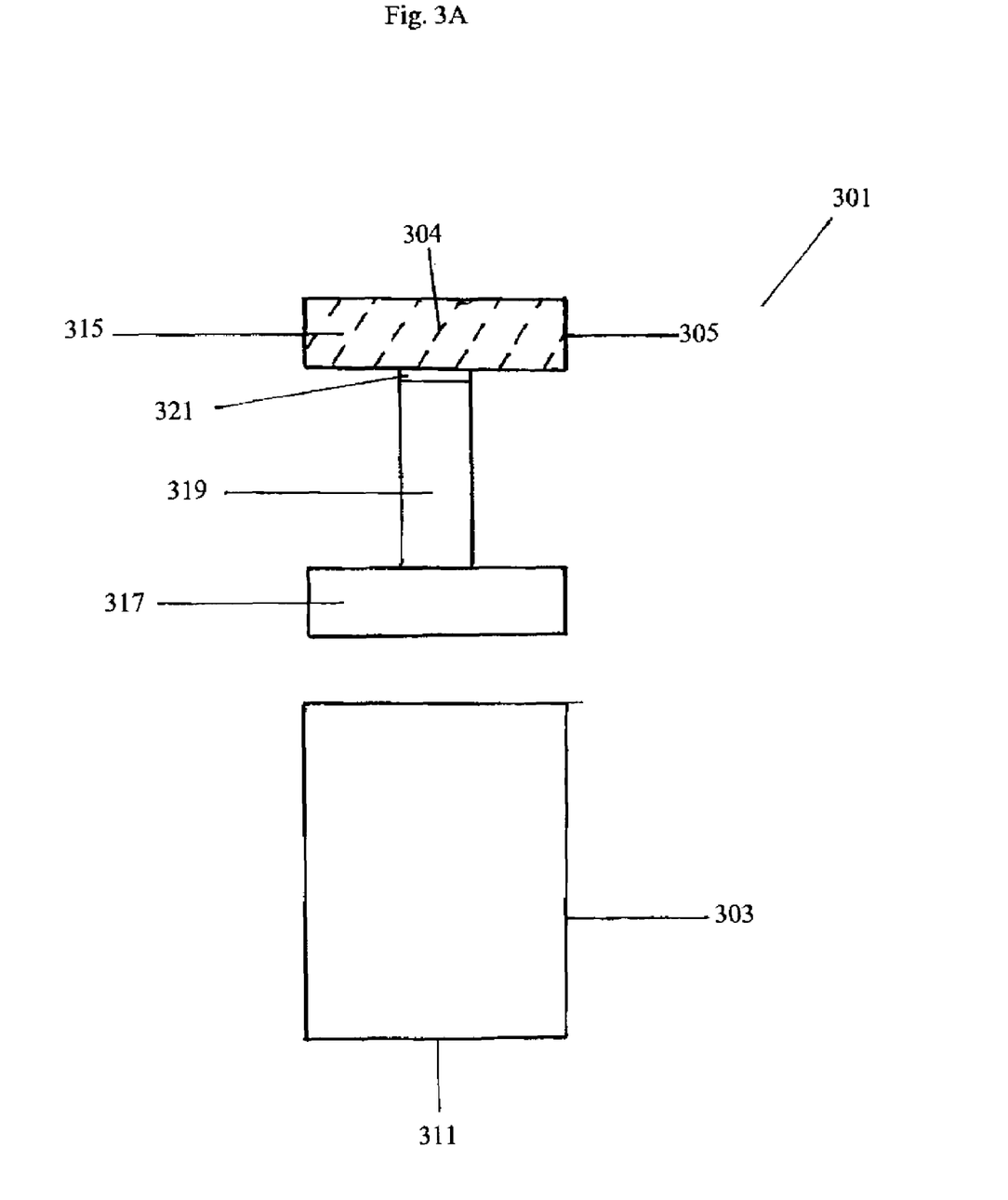
FIG. 3A is an exploded front elevation view of a vial in accordance with the present invention.
Figure 3B:
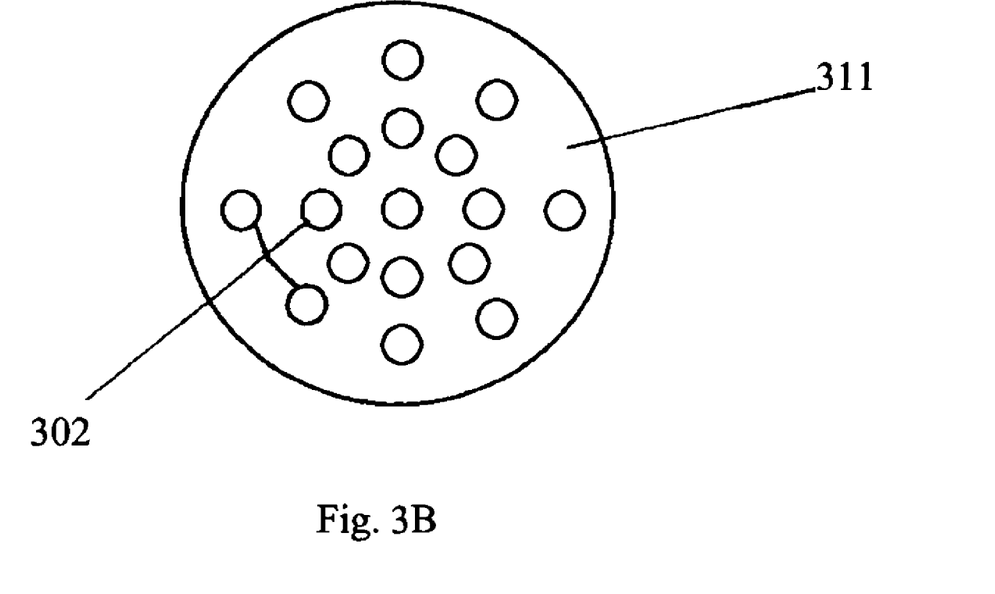
FIG. 3B is a bottom elevation view of a vial in accordance with the present invention.

FIGS. 3A and 3B depict an embodiment of a vial 301 of the present invention wherein the base 311, shown in FIG. 3B, of the container 303 is perforated with exhaust holes 302 for venting gases disposed beneath the lifting tray 317 in the container into the atmosphere when the lid 305 is being closed to container 303. In this embodiment, lifting tray 317 is acting as a piston and sealing the test strip area (i.e. the area in the container above lifting tray 317) from the gases and/or vapors below it by its interaction with the annular wall. Sealing can also be achieved through compression of a gasket disposed on the base. When vial 301 is closed the test strip area is sealed from the atmosphere outside the vial by lifting tray 317 and the top 315 of the lid 305. In this embodiment vial 301 has a desiccant 304 disposed in the top 315. Desiccant 304 may also be disposed in the lifting tray 317 provided that the lifting tray 317 provides an "air-tight" barrier with the annular wall or base from outside environment when the vial 301 is closed. The connector 319 may optionally comprise a hinge 321 disposed between the top 315 and the lifting tray 317. In FIG. 3A, hinge 321 is shown disposed at the junction of the connector 319 and the top 315.

Figure 4:
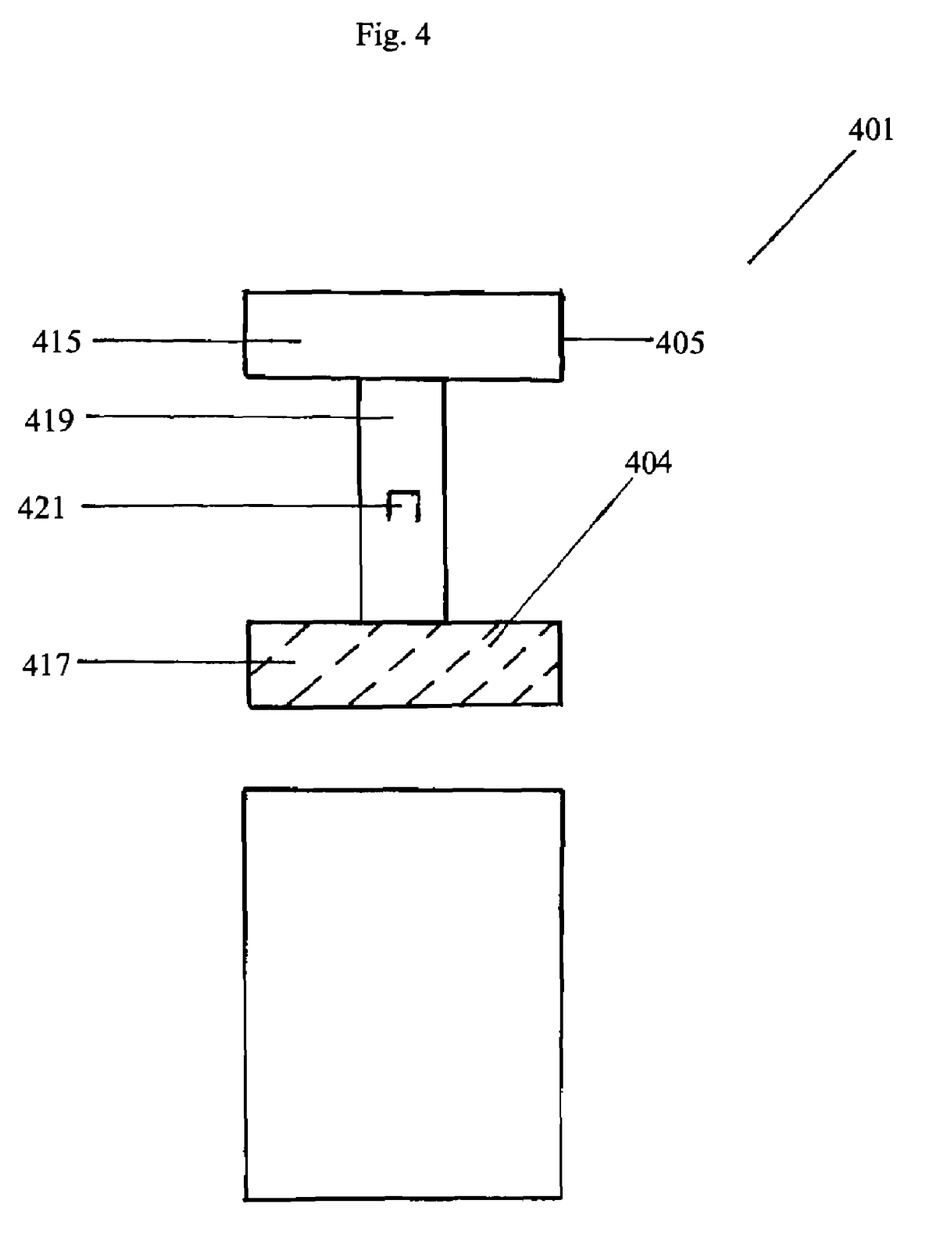
FIG. 4 is an exploded front elevation view of a vial in accordance with the present invention.

FIG. 4 shows an embodiment of vial 401 wherein the lid 405 has a connector 419 comprising a hinge 421 disposed between the top 415 and the lifting tray 417. Hinge 421 is a living hinge formed by a cut, a mold feature, or a secondary process in forming the connector 419. This figure also shows an embodiment of the present invention wherein vial 401 has desiccant 404 disposed in lifting tray 417. Openings in the top surface of the lifting tray 417 provide communication between the desiccant and the test strip area.

Figure 5:
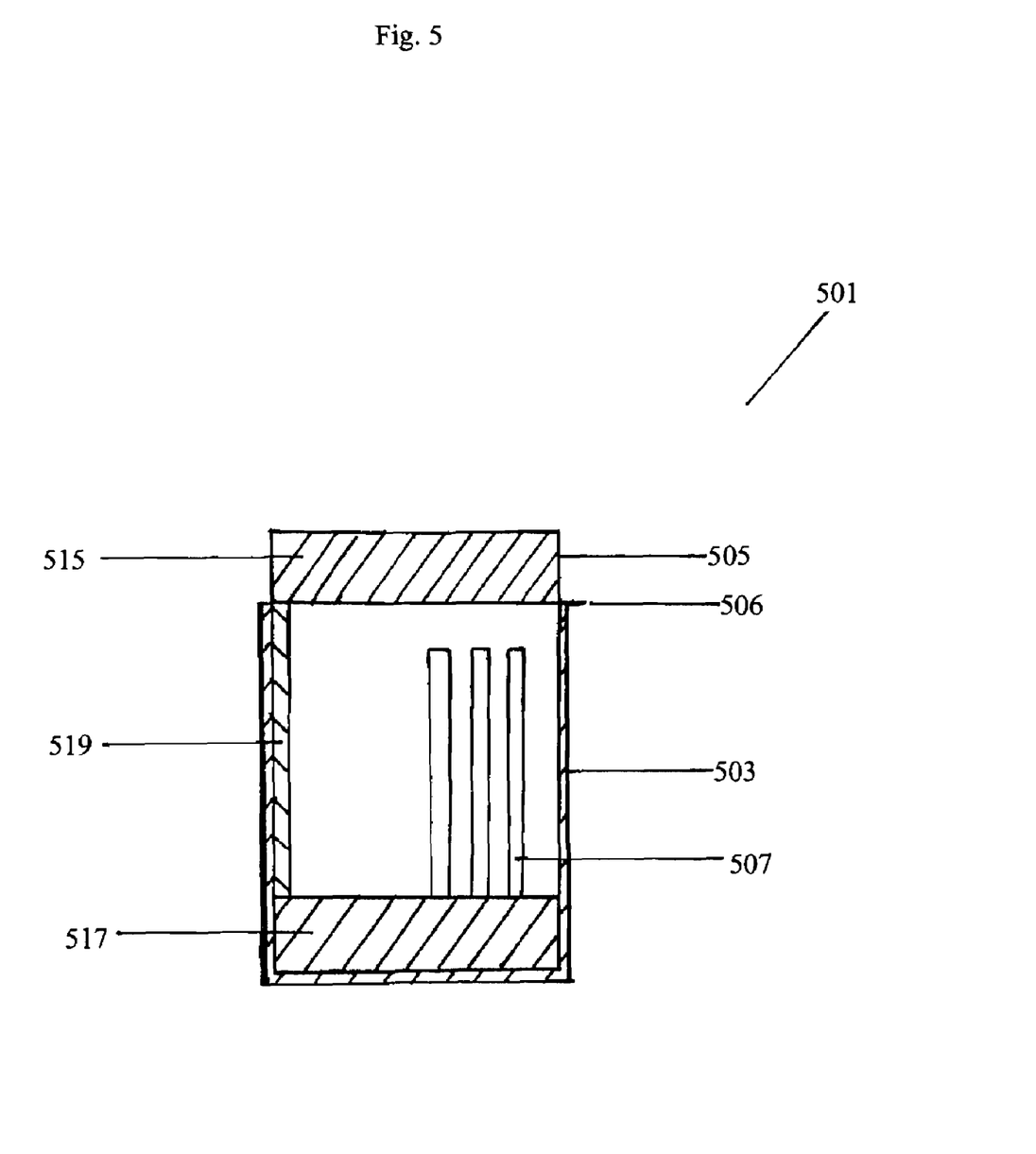
FIG. 5 is a side cross section view of a vial in accordance with the present invention.

FIG. 5 shows a side elevation cross-section of another embodiment of the present invention wherein the vial 501 is closed. The vial may comprise a feature (e.g. a depression on the container or a lip on the top) to facilitate the user's ability to easily open the vial. Here this feature is a thumb lip 506 disposed on the periphery of the top 515. The thumb lip 506 allows a user the ability to easily open the vial and remove test strips 507 therein contained. This figure also illustrates a preferred embodiment of lid 505 wherein connector 519 is connected to the top 515 and the lifting tray 517 at an edge thereof. However, the connector 519 of the present invention may be connected at any point to the top 515 and the lifting tray 517 provided that the top 515 is capable of engaging the annular wall of the container 503 for closing of the vial 501 and that the lifting tray 517 may slidably engage the annular wall. As an example the connector 519 may be connected to the top 515 at the center of the underside of the top 515 and to the lifting tray 517 at the center of its top side.

In accordance with the present invention, it is preferable that the vial further comprises a seal disposed on the lid, container, or both. Types of seals are not limited and may include gaskets, raised sealing ridges, and stoppers among other seals. In a preferred embodiment, this seal is a raised sealing ridge disposed on the lid, the container, or both and optionally further comprises a corresponding depression located on the opposite surface for snap fit engagement with the raised sealing ridge where the raised ridge snaps into the corresponding depression when the lid is closed with the container. The raised sealing ridge and the optional corresponding depression may be circular or oval in nature depending on the shape of the annular wall.

The term "snap fit engagement" is herein understood to mean the interaction between the raised sealing ridge and the corresponding depression. For example, in the embodiments where a raised sealing ridge is disposed on the inside of the lid and a corresponding depression is disposed on the outer surface of the annular wall of the container and where the lid is being closed with the container, the raised sealing ridge of the lid slides along the annular wall of the container until it reaches the corresponding depression where it is received. In a preferred embodiment when the raised ridge is received by the corresponding depression a noise is made by the interaction, for example a "click", to notify the user that the vial is sealed.

Figure 6:
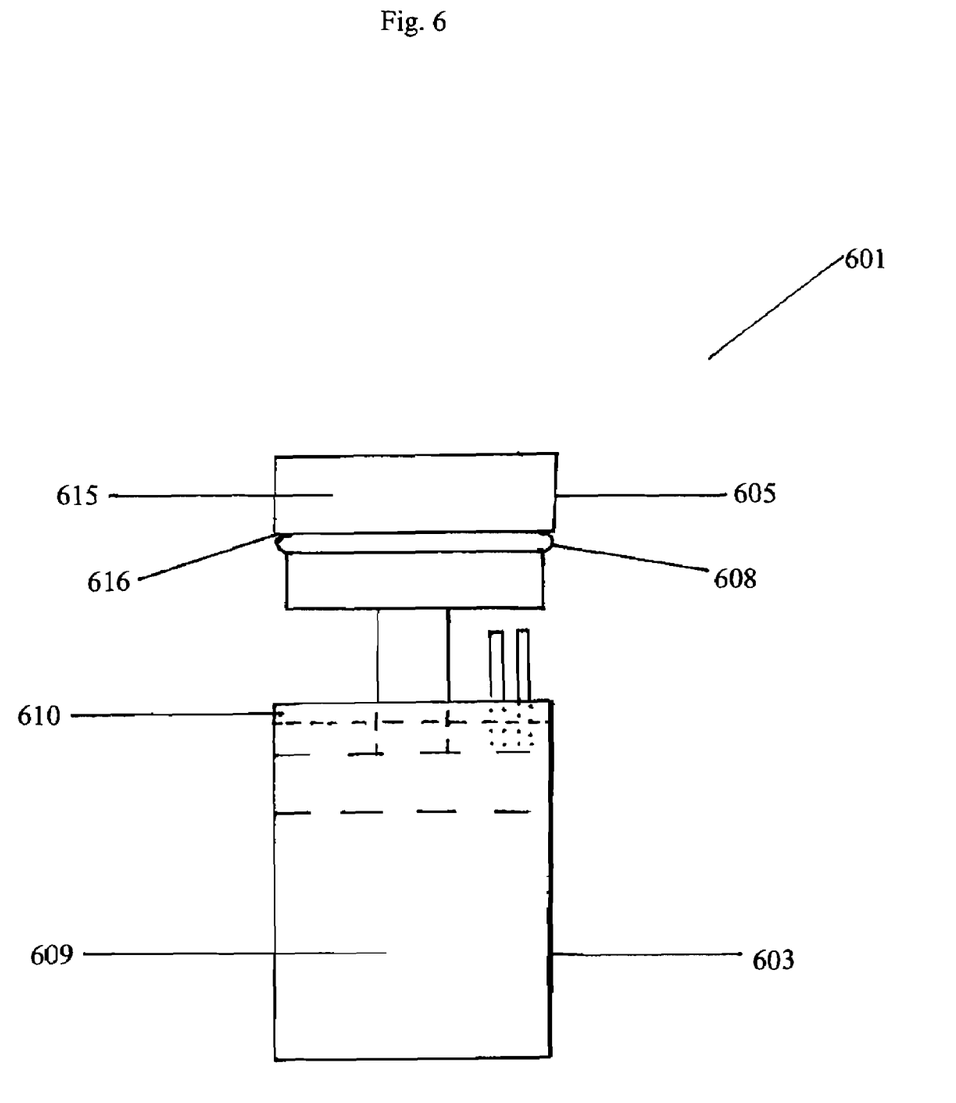
FIG. 6 is a front elevation view of a vial in accordance with the present invention.

FIG. 6 shows a vial 601 in accordance with the present invention wherein vial 601 further comprises a seal 608 disposed on the lid 605 or on the container 603 or on both. In this figure, seal 608 is a raised sealing ridge 608 disposed about the periphery of top 615. Container 603 may optionally have a corresponding depression 610 disposed on the inside of its annular wall 609 for snap fit engagement with raised sealing ridge 608.

Figure 7:
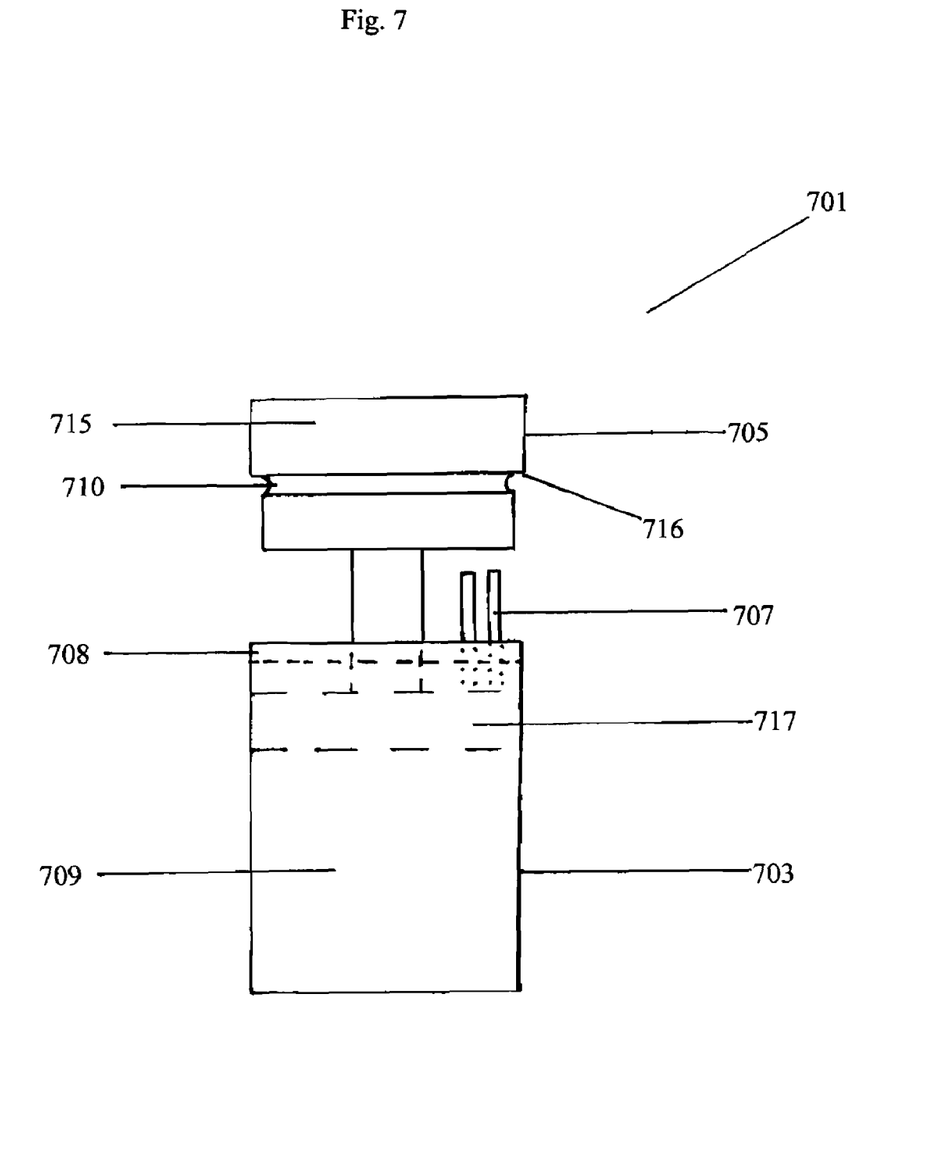
FIG. 7 is a front elevation view of a vial in accordance with the present invention.

FIG. 7 shows another embodiment of the seal 708. Seal 708 is a raised sealing ridge 708 disposed on the inside of the annular wall 709 of container 703. Top 715 of the lid 705 may optionally have a corresponding depression 710 for snap fit engagement with seal 708 when the lid 705 is closed to container 703. Test strips 707 are disposed on lifting tray 717 which is slidably engaged with annular wall 709 of container 703.

In the embodiments shown in FIGS. 6 and 7 the top 615, 715 below the raised sealing ridge 608 or depression 710 is smooth for closing engagement with the annular wall 609, but may have step region 616, 716 above the seal 608 or depression 710 so that the combination of container and lid is smooth. This step however is optional.

Figure 8:
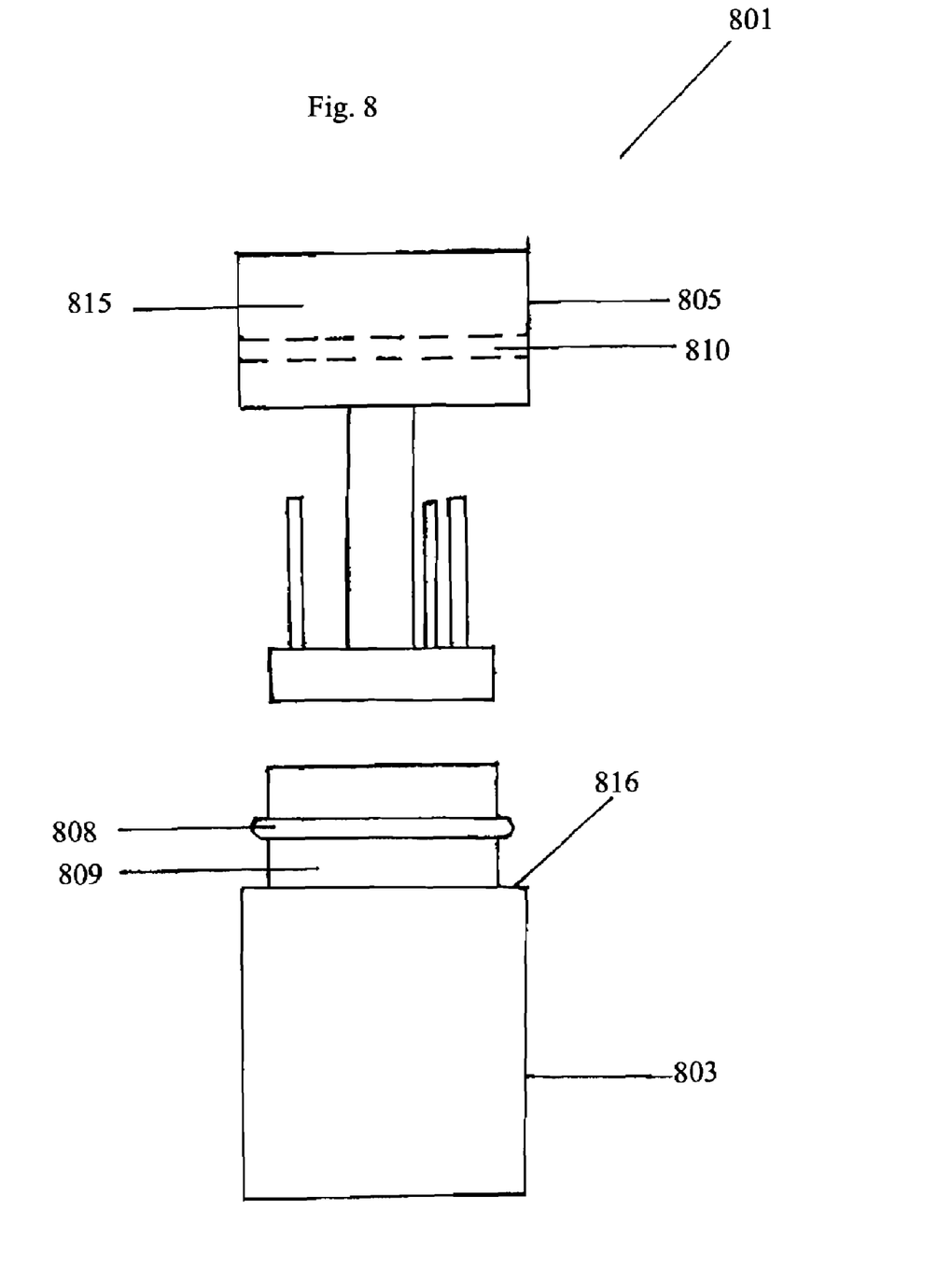
FIG. 8 is an exploded front elevation view of a vial in accordance with the present invention.

FIG. 8 shows an embodiment of vial 801 in accordance with the present invention wherein top 815 of lid 805 is sized to receive the annular wall 809 of the container 803. Container 803 further comprises a raised sealing ridge 808 disposed on the annular wall 809. Top 815 further comprises a corresponding depression 810 for snap fit engagement with sealing ridge 808. In another embodiment, the annular wall of the container maybe sized to receive the top of the lid wherein the lid, container, or both have a seal.

The term "sized to receive" as it refers to the sizing of the top of the lid or the annular wall of the container is herein understood to mean that, for example, when the top is "sized to receive" the annular wall of the container and when a user is closing the lid to the container, the top fits onto the container so that the fit between the top and the container is sufficiently tight to prevent a test strip from slipping between the top and the container and falling out of a closed vial. In a preferred embodiment the top slides onto or into the container with minimal force, for example the force applied by one hand of the user. In some embodiments, for example in the absence of a seal as depicted in FIGS. 1E, 1F, 3A, 4, and 5, the fit between the top and the container maybe sufficiently tight so as to ensure a stable humidity environment inside the vial.

Figure 9:
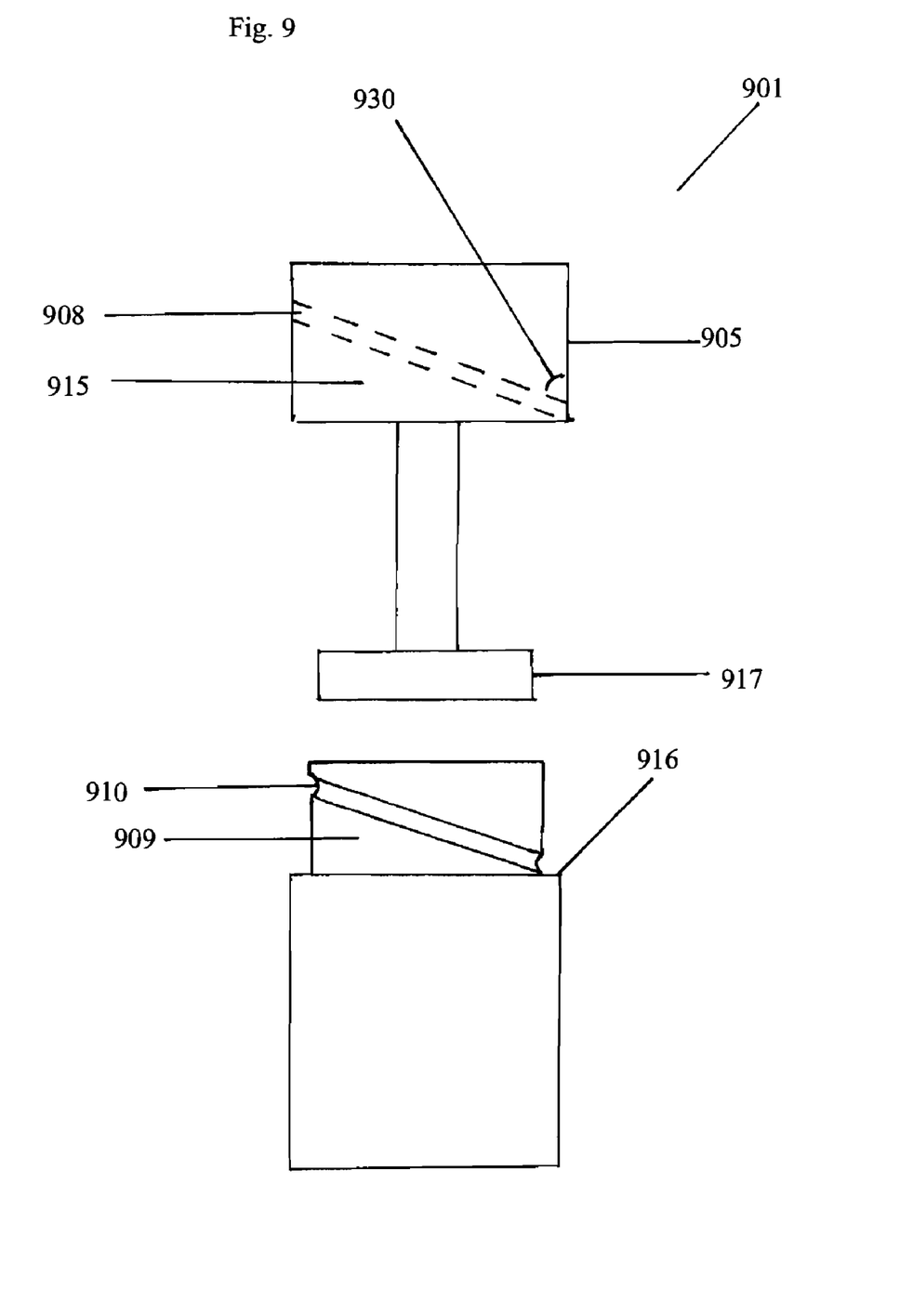
FIG. 9 is an exploded front elevation view of a vial in accordance with the present invention.
Figure 10:
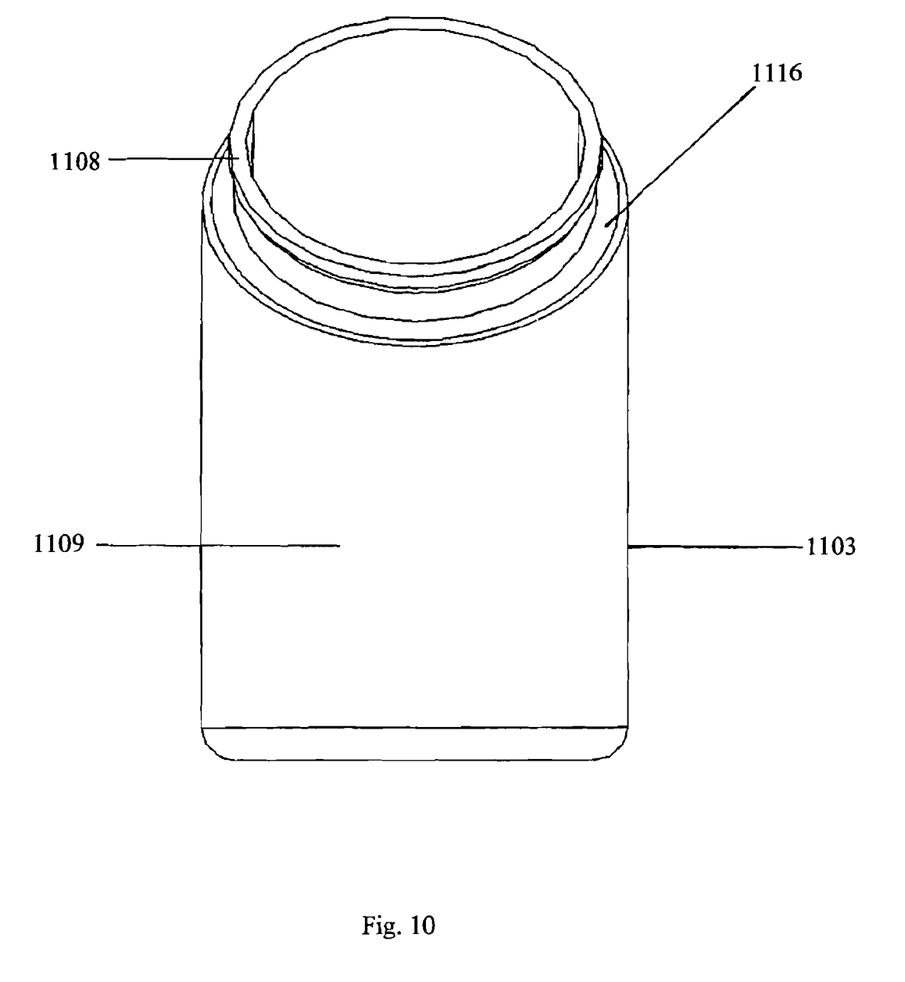
FIG. 10 is a front elevation view of a container for a vial in accordance with the present invention.

As depicted in FIGS. 9 and 10, in preferred embodiments the raised sealing ridge is circular and may be employed even if the annular wall of the container is oval. If the annular wall of the container is oval then a circular raised ridge may be employed by disposing the ridge at an oblique angle with respect to the axis of the annular wall. A circular sealing ridge provides a more rigid seal as compared to an oval ridge and is able to better withstand deformation pressures thereby providing a better seal for the vial.

FIG. 9 shows vial 901 wherein annular wall 909 is oval. Lifting tray 917 is also oval so that it may slidably engage annular wall 909. In this figure top 915 of lid 905 is sized to receive annular wall 909. Further a circular raised sealing ridge 908 is employed on the inside of top 915 even though annular wall 909 is oval. This raised sealing ridge 908 is disposed on the inside of the top 915 at an oblique angle 930 (e.g. not 90°) with respect to the axis of the annular wall 909. Oblique angle 930 is selected such that raised ridge 908 is circular. A corresponding depression 910 may optionally be employed on annular wall 909 at the same oblique angle 930 for snap fit engagement with the circular sealing ridge.

FIG. 10 shows a front view of a container 1103 with an oval annular wall 1109. Container 1103 comprises a circular raised sealing ridge 1108 disposed at an oblique angle with respect to the axis of the annular wall 1109. In the embodiments shown in FIGS. 8, 9, and 10 the annular wall 809, 909, 1109 is smooth on the inside, but may have step region 816, 916, 1116 on the outside so that the combination of container and lid is smooth. This step however is optional.

The generally annular wall of the container may be circular, elliptical or oval in shape. It is sometimes preferred that the overall vial shape and also the shape of the annular wall be oval in nature so that the vial may easily fit into a carrying case for medical supplies to be carried by a user. It is also often preferred that medical test strip vials be camouflaged or appear to be something other than what they are. For example, a user may desire to have the test strip vial be in the shape of lipstick, lip balm, eye liner, a pen, or some other indiscreet object in order to downplay what is therein contained. Thus variations of the shape of the vial and its lid and/or container of the present invention are contemplated herein and do not depart from the scope of the present invention.

The material and methods used to make the vials of the present invention are not particularly limited. However, for ease of manufacture and the costs associated therewith injection molded thermoplastic resin is often preferred.

The invention claimed is:

1. A diagnostic test strip vial comprising a container, a lid, and a plurality of diagnostic test strips, wherein:
   the container comprises a generally annular wall terminating at a base and at an open mouth at an end opposite the base,
   the lid comprises a top and a lifting tray connected to the top by a connector, wherein:
      the lifting tray is sized to slidably engage the inner side of the annular wall of the container,
      the connector is sufficiently long that the distance between the top and the lifting tray is at least as long as the length of a diagnostic test strip and sufficiently short that the top may engage the annular wall of the container to close the vial when the lifting tray is engaged with the inner side of the annular wall, and
   the test strips are disposed inside the container on the lifting tray,
   the test strips are medical diagnostic test strips used in combination with an analyte diagnostic meter for measuring the concentration of glucose in blood.

2. The vial of claim 1, wherein the annular wall of the container is oval.

3. The vial of claim 1, further comprising a seal disposed on one of the lid, the container, or both the lid and container.

4. The vial of claim 3, wherein the seal comprises a raised sealing ridge.

5. The vial of claim 4, wherein the seal further comprises a corresponding depression for snap fit engagement with the raised sealing ridge.

6. The vial of claim 4, wherein the raised sealing ridge is circular.

7. The vial of claim 1, wherein the connector comprises a hinge.

8. The vial of claim 7, wherein the hinge is disposed at a position on the connector selected from the group consisting of: at the junction of the connector and the lifting tray; between the lifting tray and the top; and at the junction of the connector and the top.

9. The vial of claim 7, wherein the hinge is a living hinge.

10. The vial of claim 1, wherein the lifting tray is perforated.

11. The vial of claim 10, further comprising a desiccant disposed below the lifting tray in the container.

12. The vial of claim 10, wherein the lifting tray further comprises a desiccant.

13. The vial of claim 10, wherein the top of the lid further comprises a desiccant.

14. The vial of claim 1, herein the base is perforated.

15. The vial of claim 14, wherein the lifting tray further comprises a desiccant.

16. The vial of claim 14, wherein the top of the lid further comprises a desiccant.

17. The vial of claim 1, wherein the top of the lid further comprises a thumb lip disposed on its periphery.

18. The vial of claim 1, wherein the vial further comprises a desiccant comprising a molecular sieve material disposed on a portion selected from one of, or a combination of, the group consisting of the inner side of the annual wall of the container, the base of the container, the top, the lifting tray, and the connector.

19. The vial of claim 1, wherein the annular wall of the container comprises a stopping ridge disposed on its inner side.

20. A diagnostic test strip vial comprising a container, a lid, a desiccant, a snap fit seal, and a plurality of diagnostic test strips, wherein:
   the container comprises a generally annular wall terminating at a base and at an open mouth at an end opposite the base,
   the lid comprises a top and a perforated lining tray connected to the top by a connector, wherein:
      the lifting tray is sized to slidably engage the inner side of the annular wall of the container, and
      the connector is sufficiently long that the distance between the top and the lifting tray is at least as long as the length of a diagnostic test strip and sufficiently short that the top may engage the annular wall of the container to close the vial when the lifting tray is engaged with the inner side of the annular wall, and
   the test strips are disposed inside the container on the lifting tray,
   the test strips are medical diagnostic test strips used in combination with an analyte diagnostic meter for measuring the concentration of glucose in blood,
   the desiccant is disposed below the perforated lifting tray in the container, in the lifting tray, in the lid, or any combination thereof, and
   the snap fit seal comprises a raised ridge on the annular wall of the container or on the top of the lid and a corresponding depression on the annular wall or the top, wherein when the top is engaged with the container, the snap fit seal seals the lid to the container by the interaction of the raised ridge and the corresponding depression.

21. The vial of claim 20, wherein the connector comprises a living hinge disposed at a position selected from the group consisting of: the junction of the connector and the lifting tray; between the lifting tray and the top; and the junction of the connector and the top.

22. The vial of claim 20, wherein the raised ridge is circular.

23. The vial of claim 20, wherein the annular wall of the container is oval.

24. The vial of claim 20, wherein the annular wall of the container comprises a stopping ridge disposed on its inner side.

* * * * *

UNITED STATES PATENT AND TRADEMARK OFFICE
CERTIFICATE OF CORRECTION

| | | |
|---|---|---|
| PATENT NO. | : 7,501,093 B2 | Page 1 of 1 |
| APPLICATION NO. | : 11/252959 | |
| DATED | : March 10, 2009 | |
| INVENTOR(S) | : Demelo et al. | |

It is certified that error appears in the above-identified patent and that said Letters Patent is hereby corrected as shown below:

Column 8, Claim 20, Lines 20 through 21 should read: -- the lid comprises a top and a perforated lifting tray connected to the top by a connector, wherein: --

Signed and Sealed this

Fourteenth Day of April, 2009

JOHN DOLL
*Acting Director of the United States Patent and Trademark Office*